United States Patent [19]

Jasinski et al.

[11] Patent Number: 5,005,406
[45] Date of Patent: Apr. 9, 1991

[54] MONITORING DRILLING MUD COMPOSITION USING FLOWING LIQUID JUNCTION ELECTRODES

[75] Inventors: Raymond Jasinski, Tulsa, Okla.; Philip Fletcher, Hardwick; Claude Vercaemer, Cambridge, both of England

[73] Assignee: Schlumberger Technology Corporation, Houston, Tex.

[21] Appl. No.: 442,954

[22] Filed: Nov. 28, 1989

[30] Foreign Application Priority Data

Dec. 21, 1988 [GB] United Kingdom ............... 8829758

[51] Int. Cl.$^5$ ............................................. E21B 47/00
[52] U.S. Cl. ...................................... 73/153; 324/370
[58] Field of Search ................. 73/153, 155; 324/369, 324/370; 175/40

[56] References Cited

U.S. PATENT DOCUMENTS 4,154,659  5/1979  Zetter ................................. 204/1 T
4,904,603  2/1990  Jones et al. ...................... 73/153 X

FOREIGN PATENT DOCUMENTS 0262582  9/1987  European Pat. Off. .
0282231  9/1988  European Pat. Off. .
1558817  10/1976  United Kingdom .

OTHER PUBLICATIONS

"Influence of Colloidal Charge on Response of pH and Reference Electrodes: The Suspension Effect", Pergamon Press, by Donald P. Brezinski.
"Ion-selective Electrodes", Cambridge University Press, by Jiri Koryta et al.
"A System for Continuous On-site Measurement of Sulfides in Water-base Drilling Muds", SPE-6664, by David M. Hadden.
"Reference Electrodes with Free-flowing Free-diffusion Liquid Junction", Analytical Chemistry, 1986, 58, 2585-2589, by Rene E. Dohner et al.

Primary Examiner—Jerry W. Myracle
Attorney, Agent, or Firm—Henri Dupont; John J. Ryberg

[57] ABSTRACT

In the rotary drilling of oil wells a drilling mud is used both to transport the cuttings up to the surface and to impose an hydrostatic pressure on the walls of the borehole. For these functions the mud must for example have an acceptable density and viscosity. It is therefore important to monitor the characteristics of the mud, and to keep them within certain limits. The technique proposed involves the use of an ion selective/reference electrode pair to measure in the mud the potential of the selected ion (as a potential difference), and thus allow a determination of that ion's concentration. Thus, it is a method in which, using a selective/reference electrode pair where the reference electrode is of the type having a liquid junction via an aperture within the reference electrode containment vessel, there is determined the potential difference generated by, and thus the concentration of, the ion in the mud. However, the nature of drilling mud is such that some undesirable interaction between the mud components and the reference electrode occurs, possibly leading to erroneous results. The invention suggests that this problem can be dealt with if, during the determination, the electrolyte constituting the reference electrode's liquid junction is caused to flow through the electrode containment vessel's aperture and out of the vessel into the mud.

7 Claims, 2 Drawing Sheets

MONITORING DRILLING MUD COMPOSITION USING FLOWING LIQUID JUNCTION ELECTRODES

This invention relates to the monitoring of drilling mud, and concerns in particular a method for monitoring changes in the chemical composition of the mud.

In the rotary drilling of wells, such as hydrocarbon (oil and gas) wells, a mud is continuously circulated from the surface down to the bottom of the hole being drilled and back to the surface again. The mud—usually a fluid mixture of a clay such as bentonite suspended in a continuous phase such as water—has several functions. One of these is to transport the cuttings drilled by the drill bit up to the surface where they are separated from the mud. For this purpose the mud must be viscous enough to entrain the cuttings yet fluid enough to pump. Another function is to impose an hydrostatic pressure on the walls of the borehole so as to avoid a collapse of the borehole and an influx of gas or liquid from the formations being drilled. For this function the mud must be dense enough to resist formation pressure, yet not so dense that its pressure forces it deep into the formations, possibly fracturing them. It is therefore important to monitor the characteristics of the mud, and to keep them within certain limits. Weighting materials, barite for example, are added to the mud to make it exert as much pressure as needed to contain the formation pressures. Numerous chemicals are available to give the mud the exact properties it needs to make it as easy as possible to drill the hole, and the importance of the mud, and the difficulties of controlling its composition directly in the field, can be fully appreciated.

It is known that during the drilling process the ionic composition of the drilling mud changes from its original formulation. These changes in composition are in part a measure of the downhole processes which may be termed mud-rock interactions. An important example of mud-rock interactions is ion exchange between cations in the mud and in shale formations. Until recently drilling practice has not required the ionic composition of the mud to be monitored, so that the extent of these interactions has not been determined, and the composition of the drilling mud has not been accurately maintained. However, in the Specification of our published application for European Pat. No.: 0 282 231 we have described how important such a monitoring process is, and how useful it can be. In general, in that Specification we described a method for controlling the drilling of boreholes by determining the ionic compositions of the drilling muds and/or drilled cuttings in order to monitor various chemical processes which occur in the wellbores, e.g. salt water influxes, changes in the solubility of salts with changes in pH, and cation exchange processes involving the cations added to the water-base mud (e.g. potassium, calcium) to stabilise shale sections.

More specifically, in this earlier Specification we have described and claimed a mud control method in which the mud is sampled and its aqueous filtrate is analysed at the rig site by ion chromatography for determining selected positive and negative ion concentrations. In addition, the pH and the temperature of each sample may be measured. In a preferred embodiment, the anion, monovalent cation and divalent cation contents of the mud sample filtrate are determined by three chromatography units. Preferably, the composition of the mud filtrate thus monitored is interpreted to indicate downhole interactions, with the composition of the mud supplied to the hole being adjusted to or towards the optimum as drilling proceeds.

The method of the aforementioned European application preferably involves the use of ion chromatography to determine the nature and quantity of the various ionic mud components, and within the expected bounds it works well. However, ion chromatography as a technique is not best suited for application outside a laboratory, and its employ on an oil drilling rig can be a little difficult, even when automated as fully as possible. There has thus been proposed a different approach to the determination of the ionic mud components, one that is simpler and more "robust"—and therefore better suited to the on-site conditions where it is likely to be needed. Specifically, it has been suggested that use may be made of the known electrical potential generating effect of an ion in solution in contact with an appropriate electrode, and of the fact that this potential is indicative of the concentration of the "selected" ion in the solution. Thus, the measurable difference between the two potentials generated at an electrode selective for a particular ion and at a reference electrode is similarly indicative of the selected ion's concentration (the relationship between the potential difference and the concentration is of the form Potential Difference = Constant + 60/ion
valency × log$_{10}$(ion concentration)

which is a version of the Nernst equation).

Thus, it has been proposed that the nature and quantity of each ionic mud component be ascertained by using a suitable ion selective electrode/reference electrode pair to measure the potential difference set up by the "selected" ion, and so allow a calculation of that ion's concentration in the mud. Indeed, such a selective/reference electrode pair technique has already been employed in this and other fields (notably in the analysis of materials as diverse as soil and blood, though recently a version has been suggested specifically for indicating the presence of sulphide ion in oil drilling muds). There is, however, a problem with this proposal which relates to the nature of the reference electrode and the fact that the liquid the ionic content of which is to be determined is a drilling mud—a mixture of many material sin particulate form, some of which are clays in suspension.

A common, and perfectly acceptable, form of reference electrode is a metal in contact with one of its salts which in turn is in electrical contact with the solution to be determined via an intervening electrolyte connector that does not itself give rise to an additional ion-specific potential at the liquid-sample interface. A typical example is the well-known calomel electrode (metallic mercury/mercurous chloride) with an aqueous potassium chloride "bridge" directly to the "unknown" solution; another is a silver/silver chloride electrode, also with an aqueous potassium chloride bridge directly in contact with the "unknown" solution. One convenient way in practice to achieve the desired liquid/liquid contact, or junction, between the bridge electrolyte and the unknown solution is to employ a containment vessel for the reference electrode that has a small aperture through which the liquid bridge electrolyte inside may physically contact, and thus electrically connect to, the unknown solution liquid outside. When the reference electrode is then placed in the unknown solution the aperture in the vessel allows direct contact between the two solutions (but without any significant flow of one into the other). The aperture may be filled with a porous partition (the better to minimize liquid flow through the hole), or it may simply be a very narrow, but preferably quite long, slit—like the annular gap around a "badly fitting" plug, bung, cap or lid.

Now, it has been found that, if such an apertured vessel reference electrode is used as one half of the selective/reference electrode pair, to determine the potential, and thus the concentration, of the selected ion in a drilling mud mixture, the results obtained are very significantly different from what they ought to be—for some known muds the results were from around 50% to 100% higher than those expected. It is not clear why this increment in the measured potential difference should occur, but one possible explanation is that the mud particles (which are usually electrically charged) diffuse into, and partially block, the reference electrode's vessel's aperture, thus creating what is in effect a semi-permeable membrane—specifically a "Donnan" membrane that selectively allows the passage of one charge types rather than the other—and so seriously alters the operation of the reference electrode, and as a consequence distorts the results. A similar problem has in fact been met in some other areas where reference electrodes are used in liquids containing suspended particulate matter (blood samples, and other body fluids), and a similar theory has been put forward to account for it.

Whatever the actual reason (or reasons), the theory as to what might be causing the effect in these other areas has been there used to suggest a "cure", which is that the bridging electrolyte solution used by the reference electrode should be encouraged to flow through the vessel and out via the aperture in order to prevent mud particles from diffusing into, and thereby blocking, the aperture (and to sweep out any that do). The proposed "flowing liquid junction" seems to work, and to enable the correct results to be obtained—and, somewhat surprisingly, a cure for a problem met in the analysis of a body fluid such as blood appears to be equally applicable to the very different liquids encountered in drilling muds.

In one aspect, therefore, this invention provides a method for the determination of a chosen ionic component of a drilling mud, in which, using an electrode selective for the chosen ion together with a reference electrode of the type having a liquid junction formed by a liquid electrolyte connectable via an aperture within the reference electrode containment vessel, there is determined the potential difference generated across the two electrodes by the ion in the mud, and thus there is determined the concentration of that ion in the mud, and in which, during the determination, the electrolyte constituting the reference electrode's liquid junction is caused to flow through the electrode containment vessel's aperture and out of the vessel into the mud.

The ionic components of a drilling mud may be ions of many types, in many forms. The principal ones of interest, however, are the potassium, sodium, calcium and magnesium cations, and the chloride, sulphate and bromide anions—and the carbonate and bicarbonate anions.

The method of the invention appears to be applicable to the determination of any variety of water-based (as opposed to oil-based) drilling mud. A typical water-based mud—and hereinafter references to mud are to water-based mud, unless some other meaning is clearly intended —is one that is essentially a suspension of a bentonite clay in water (usually sea water, where the drilling takes place off shore) together with various additives for viscosity, pH and density control. For example, such a bentonite/sea water mud might contain the components in Table I below.

TABLE I

| Seawater-dispersed Mud | | |
|---|---|---|
| Component | Function | Amounts (Kg/m$^3$) |
| bentonite | primary viscosifier | 36 |
| XC-polymer | viscosifier | 1 |
| CMC low viscosity | fluid loss control | 10 |
| CMC high viscosity | viscosifier, fluid loss | 2 |
| chrome lignosulphate | dispersant | as req. |
| sodium hydroxide | pH control | 3 |
| sodium carbonate | calcium control | 0.9 |
| barite | mud density | as req. |

CMC is CarboxyMethyl Cellulose.

XC is a polysaccharide produced by the action of the plant pathogen Xanthomonas Campestris on carbohydrates.

Other common types of mud contain the components shown in Table II below.

TABLE II

| Component | Function | Amounts (Kg/m$^3$) |
|---|---|---|
| Freshwater-dispersed Mud (Density = 1,500 Kg/m$^3$) | | |
| bentonite | primary viscosifier | 57 |
| chrome lignosulphate | dispersant | 9 |
| lignite | dispersant/thinner | 6 |
| sodium hydroxide | pH control | 3 |
| barite | weighting agent | 600 |
| Potassium/Polymer Inhibitive Mud (Density = 1,500 Kg/m$^3$) | | |
| bentonite | primary viscosifier | 45 |
| CMC low viscosity | fluid loss control | 1.5 |
| potassium hydroxide | potassium/pH control | 4.5 |
| XC-polymer | shale inhibition | 9 |
| calcium hydroxide | calcium control | 13 |
| barite | weighting agent | 600 |

The method of the invention starts, naturally, by suitably placing the electrode pair in the mud (it would be possible to take from the system a sample of mud, but it is more convenient to position the electrodes in the mud as it circulates in the system). In principle this placement can be made anywhere in the system, but in general it is most convenient to position the electrodes in the return mud after it has just emerged from the bore (and the cuttings separated off). For checking purposes, it may be advantageous additionally to test the mud just before it is re-circulated back down into the bore (after any additive treatment). Data from the first of these provides information about what is happening to the mud down hole, whilst data from the second provides a check that the subsequent treatment did, as was intended, restore the mud to its optimum composition. In practice, the first measurement is conveniently taken immediately below the shale-shaker, and the second is taken either downstream from the active tank or in the flow line to the drill pipe.

Figure 1:
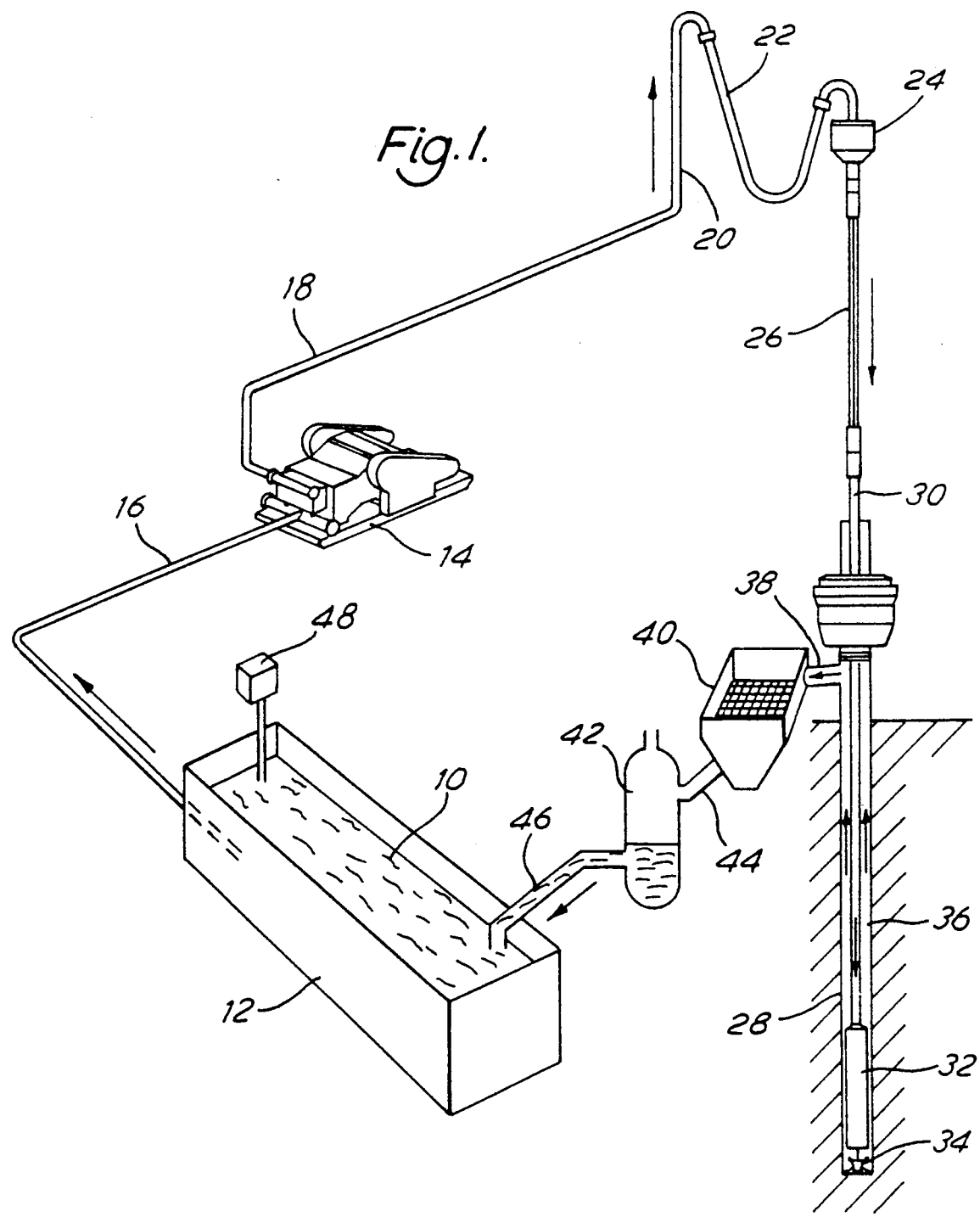
FIG. 1 shows the mud circulation equipment.

The matter will, perhaps, be most clearly understood from a consideration of FIG. 1 of the accompanying Drawings.

The mud 10 is contained in a mud pit 12, called the active tank. A pump 14 draws up the mud from the pit through a pipe 16, and forces the mud through the discharge line 18, the stand pipe 20, the rotary hose 22 and the swivel 24. The mud then flows into the kelly 26 and down the borehole 28 in the drill pipe 30 and the drill collars 32. The mud reaches the bottom of the hole at the drill bit 34, and then flows up to the surface in the annulus 36 and in the mud return line 38. The mud then falls over a vibrating screen-like device 40, called a shale shaker.

The role of the shale shaker is to separate from the liquid phase of the mud the cuttings drilled by the bit 34 and transported up in the annulus by the mud. The separation is made by having the mud pass through a screen which vibrates. The solids (called the cuttings) which are larger than the mesh size of the screen don't pass through the screen, and are rejected either in a reserve pit (when the drilling rig is on land) or in a barge (when the drilling operations are conducted offshore). The solid particles contained in the mud which have a size smaller than the mesh size of the screen pass through the screen, and therefore remain in the mud. These fine solids (hereinafter referred to as the mud solids or the solids) comprise part of the weighting material added to the mud to reach a certain mud density, as well as fine solids from the formations traversed by the borehole.

After the shale shaker 40, the mud flows into the solids control equipment, represented schematically by 42, through the pipe 44. The solids control equipment 42 could include a degasser, a desilter and a desander (these are not shown separately here). Then the mud falls into the pit 10 through the pipe 46. A mud-mixing hopper 48 is generally used to add solid materials like clay and barite to the mud in the active tank.

In the practice of the invention, mud readings should be taken (continuously) from the active tank 12 (and possibly also from the pipe 44 between the shale shaker 40 and the solids control equipment 42).

The method of the invention requires the use of an electrode selective to the ion to be determined. In general, there are several different types of selective electrode—that is, ways of constructing an electrode so that is is selective for a particular ion—as will be understood from the following description.

Ion selective electrodes are based on an ion exchange process occurring at the interface between the electrode and the fluid phase containing the ionic species being measured. This ion exchange process generates a separation of electrical charges (ions of one charge on the solid surface and ions of the opposite charge in the fluid), and thus an electrical potential. It is this potential that is actually measured (relative to some reference potential).

The ion exchange surface can be a glass membrane (such as is used for the ubiquitous glass pH electrode), or a "solid state" membrane, commonly a crystal of an insoluble salt involving the ion being sensed (e.g., silver chloride, AgCl, or lanthanum fluoride, $LaF_3$), or a liquid containing a chemical which will interact with an ion in solution—the liquid being immobilised in an otherwise inert plastic membrane or porous diaphragm.

The selectively of the ion selective electrode depends on the inherent selectivity of the ion exchange process of the membrane (of whichever sort). For example, certain glasses will ion exchange with hydrogen ions and ignore sodium ions, whilst other glasses will do the opposite—ion exchange sodium ions and ignore hydrogen ions.

The most common configuration for an ion selective electrode is that of a tube, typically a tube nominally 12 cm long and 1 cm in diameter. The sensing membrane is hermetically sealed to one end of the tube. Electrical contact is made to the side of the membrane inside the tube, commonly in one of two ways. The first is contact via an ionically conducting fluid. Here, the tube is filled with a solution containing an electrolyte—for example, 3.8 molar potassium ions and chloride ions; this solution is variously called the "bathing" or "bridging" solution as well as the "filling" solution. A wire—of silver, say—is placed into this solution such that it protrudes out of the tube at the non-membrane end (and is usually sealed in to prevent spillage). It has been found that the performance is improved if the portion of the wire contacting the bathing solution is coated with a substance that ion exchanges with the filling solution. An example of this type of electrode is silver chloride-on-silver, in contact with potassium chloride filling solution.

The second form of electrical contact to the sensing membrane is via direct physical contact with the wire—i.e., in the absence of any bathing solution. This is commonly called an "ohmic" contact. It is generally used for the solid state sensors, though it can be used with liquid membrane sensors as well. A variation of this ohmic contact method is a wire coated directly with the sensing liquid-filled plastic.

The term "ion selective electrode" is nowadays also used to describe devices configured as just described but with an extra solution and a chemically active membrane intervening between it and the test solution. One such layer can be a membrane selectively permeable to carbon dioxide. Here the $CO_2$ passes through the membrane and dissolves in the intervening fluid phase, which is also contacted by a pH electrode. The pH change in this intervening solution is sensed, and is proportional to the amount of $CO_2$ present in the original fluid phase. Biologically active chemicals have also been used in the intervening membrane to convert the substance being sensed (e.g., glucose) into a pH-altering chemical.

Available selective electrodes may be of one or other of these types. For example, some of the commercially-available electrodes that are selective for sodium, potassium, calcium, chlorine and sulphur are those in Table III below.

TABLE III

| Ion | Name | Electrode Type | Manufacturer/Supplier |
|---|---|---|---|
| Sodium ($Na^+$)* | EIL Na+ | glass | Kent Industrial |
| Sodium ($Na^+$)* | Phillips 1S 561 | membrane | Phillips |
| Sodium ($Na^+$)* | *1SE 315/R | glass | Russell pH Ltd |
| Sodium ($Na^+$)* | Orion 941100 | solid state | Orion Research |
| Sodium ($Na^+$)* | *Orion 971100 | glass | Orion |
| Potassium ($K^+$) | Phillips 1SE 561 | membrane | Phillips |
|  | *Orion 93 series 1SN NQ1 | PVC | Orion |
|  | *EIL $NH_4/K^+$ | glass | Kent |
| Calcium ($Ca^{++}$) | Russell 1SE 310 | PVC | Russell |
|  | *Phillips 1SE 561 | membrane | Phillips |
| Chlorine ($Cl^-$) | Russell 1SE 301 | solid state | Russell |
|  | *Phillips 1S 560 | solid state | Phillips |
| Sulphur ($S^=$) | Russell 1SE 305 | solid state | Russell |

TABLE III-continued

| Ion | Name | Electrode Type | Manufacturer/ Supplier |
|-----|------|----------------|------------------------|
| | *Orion OR941600 | solid state | Orion |

Of these, those marked with an asterisk (*) seem to be especially suited for use in the proposed method.

The method of the invention also requires the use of a reference electrode of the type having a liquid junction via an aperture that allows direct liquid-liquid contact but normally restricts any flow of bridge electrolyte liquid from the reference electrode into the unknown solution (the mud). Here, too, there are several different types of electrode system, both as regards their electrode materials (as in calomel or in silver/silver chloride) and as regards the nature of their liquid junction, as now explained.

Commercially-available reference electrodes are similar in physical configuration to the "bathing" solution ion selective electrode described above. The major difference occurs at the junction of the reference electrode and the fluid being measured. The reference electrode is designed to contact directly the inner bathing solution with the fluid phase being measured. In effect, the sensor membrane is replaced with a glass frit, porous ceramic plug, or glass-sealed fibre.

The reason for effecting liquid-to-liquid contact is either (a) to minimize, if not eliminate, the electrical potential difference between the reference electrode metal/salt film and the test solution, or (b) at least to keep this potential difference constant over the ion concentration range being measured.

The most common reference electrodes are based on silver wires in contact with silver chloride salt, or with metallic mercury and mercurous chloride (calomel). The bathing solutions are generally potassium chloride salts dissolved in water. All these, and many less widely used reference electrodes, are described in D. Ives and G. Janz, "Reference Electrodes", 1961, Academic Press, New York.

Examples of available and suitable reference electrodes are the Radio meter K201 and Metrohm Double Junction.

In order for the potential difference output of the selective/reference electrode pair to be acceptably accurate, and so useful in allowing a determination of the concentration of the chosen ion, it is necessary to cause the bridging liquid electrolyte within the reference electrode vessel to flow through the aperture. The actual "pumping" of this liquid (from some suitable reservoir—possibly the electrode vessel itself) may be accomplished in any convenient way (such as by a simple gravity feed), and needs no further discussion here. However, the rate at which the liquid flows does need some comment.

In keeping with the theory that the "false" readings obtained without liquid flow are caused by mud particles diffusing into, and "blocking", the aperture, it has been found that for any given reference electrode (with an aperture of a particular size) there is an absolute minimum flow rate; this is necessary, presumably, to sweep the mud particles out of, and away from the aperture. This minimum flow rate seems, as might be expected, to be higher the larger the area of the aperture. Thus, it is not possible to give any general guidance on minimum flow rates, but only to indicate what rates have been found satisfactory for specific electrodes. For the Radiometer K201, for example, a desirable flow rate was as high as 6 ml/hr, while for the Metrohm Double Junction device a flow rate as low as 0.07 ml/hr seemed acceptable. This uncertainty in minimum flow rates is not a problem, however, because for any particular reference electrode it is merely a matter of routine experimentation to discover below what rate the observed results become erroneous, and then in practice always to exceed that rate by a comfortable margin.

Figure 2:
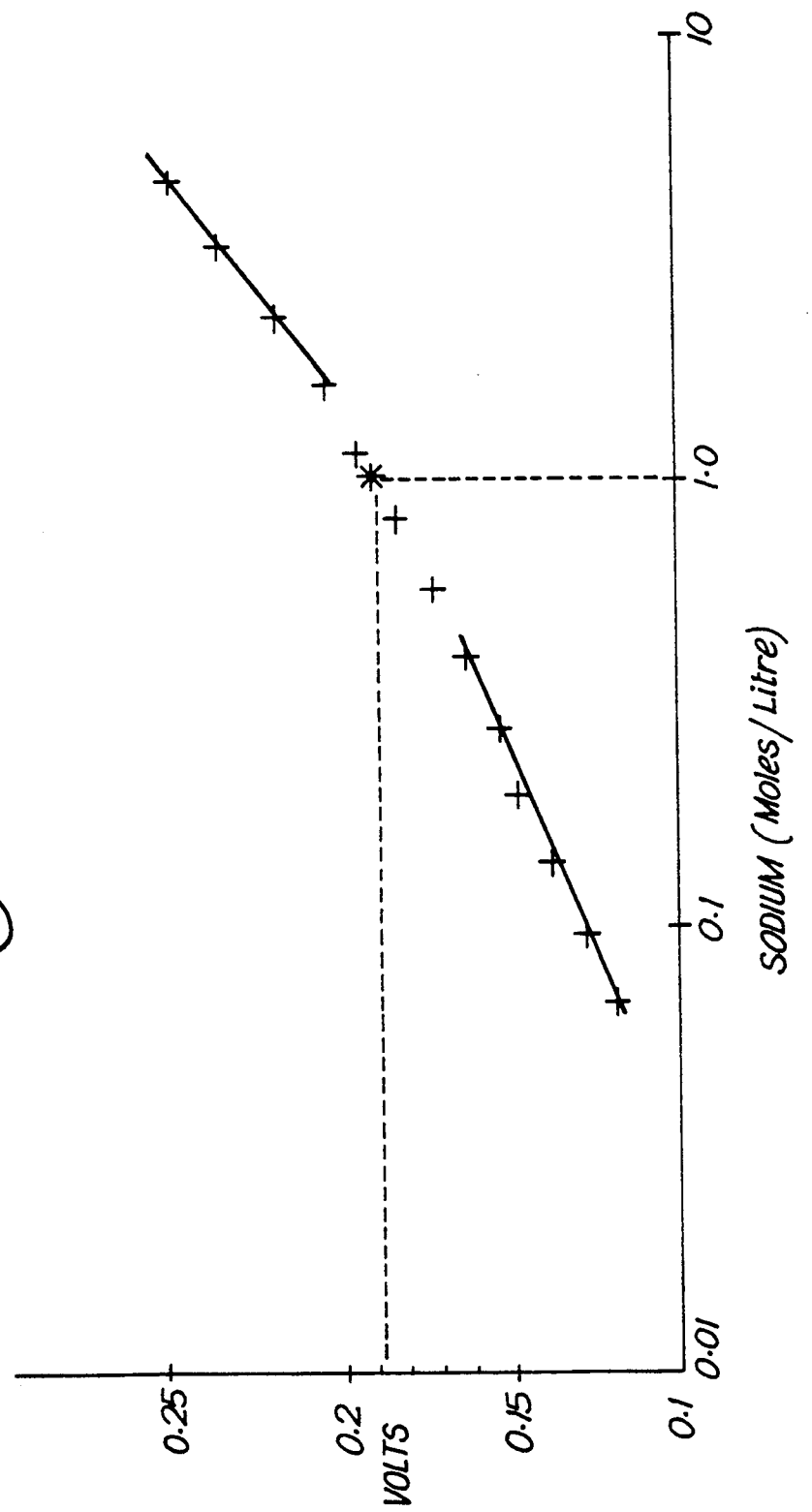
FIG. 2 shows a sodium ion calibration curve.

Once the potential difference for the chosen selective/reference electrode pair has been measured it is a relatively simple matter to determine the ion's concentration. For example, this may be done from a calibration curve: the electrode pair is first "tested" on a whole series of known ion concentrations (the procedure is discussed in more detail hereinafter), and the results plotted to give a graph of the potential difference against concentration, from which may then be read directly the ion concentration corresponding to the potential difference observed for the "unknown" mud. A particular such calibration curve (for the sodium ion, and based upon data obtained from a sodium glass-silver/silver chloride selective/reference electrode pair) is shown in FIG. 2 of the accompanying Drawings. The Calibration Values are marked with a cross (+), and it will be clear that the "unknown" value potential difference of 0.19 millivolts, marked with an asterisk (*), corresponds to a concentration of 1.0 moles/liter.

Alternatively, there may be employed the Nernst-derived equation referred to above, $$PD = K + 60/v \times \log_{10}([I])$$

(where PD is the measured potential difference in millivolts, K is a constant the value of which is determined by previous tests, v is the valency of the ion concerned, and [I] is the molar concentration of the ion).

K is constant throughout the calibration procedure and throughout the measurement. It is a function of the particular chemistry of the reference electrode, the composition of the "bathing" solutions, and certain physical properties of the sensing membrane. It is the major variable determined by the calibration procedure. v is the valence of the ion being measured—e.g., +1 for the sodium ion, and +2 for the calcium ion. The number 60 is nominal so that for greatest accuracy the term given here as 60/v is best determined by the calibration procedure. Thus, calibration equates the measured potential and the logarithm of the concentration in terms of a constant K and the slope 60/v of a line. For greater accuracy this line can be replaced by a second order polynomial to take into account curvature of the type shown in FIG. 2 (in which, as can be seen, a change in potential of 60 millivolts means a molar concentration change of one order of magnitude).

In the present invention, a mud filtrate ion may be a "principal" ion, and of interest for one or more of a number of reasons. For example, it may have a concentration in the mud of at least 100 ppm. It may have a significant effect on mud properties at any concentration, which is frequently the case when it is a deliberate special additive to the mud. It might be one giving rise to potential environmental problems if discharged even at low concentrations—e.g., well below 100 ppm. All mud filtrate ions of interest could be assessed by the method of the invention, but are not necessarily so assessed. Thus, hydrogen and hydroxyl ion concentrations can be provided by pH measurement, and carbonate and hydrogen (bicarbonate) ion concentrations can be deduced from the measured concentrations of other ions. Of the principal mud filtrate ions present which are suitable for the inventive method, not all need to be measured, though at least one cation concentration and at least one anion concentration are measured in this way. Typical principal mud filtrate ions for assay by this technique are sodium, potassium, calcium, sulphur and chlorine.

As explained in detail in our aforementioned European application, the assessment of the original mud components based upon the determined ion concentration values is most conveniently made part of a larger system that outputs recommendations as to how the actual, present, mud components should be modified to attain the optimum values for the conditions currently being encountered down hole. More specifically, the measurement of the ionic composition of the mud filtrate is accompanied by a rig-site, computer-based interpretation giving continuous information on the chemical composition of the mud and the extent of the mud/formation interactions; this is associated with an advisory module recommending appropriate changes in the mud formulation.

EXAMPLES

The following Examples are now given, though by way of illustration only, to show details of various embodiments of the invention.

Calibration

Ion selective electrodes are calibrated with the electrical potentials of the ion selective electrode-reference electrode pair measured when they are immersed in suitable salt solutions of known but different compositions (for the systems described herein these salt solutions do not contain suspended solids such as clay particles). The measured potentials (in volts) are then plotted against the logarithm of the concentration of the ion being sensed. The resulting plot, or curve, is the calibration curve. In practice it may be convenient then to fit each produced curve to an equation (the standard deviation of regression of the curve fit is then a quantitative measure of how good the fit is—how accurately the equation may be used to convert real potential measurements into ion concentrations).

In general, it is found that the accuracy of the calibration is improved if the concentrations are expressed in terms of ionic activity rather than ionic molarity.

When actually using the thus-calibrated electrodes, electrical potential measurements are made with them in the fluid of unknown composition, using the flowing reference electrode. The measured potential is then compared with the calibration curve (or with the equation fitted thereto), and the concentration of the ion of interest so determined.

EXAMPLE 1

Electrical potentials were measured between a Metrohm sodium ion selective electrode (No. 6.0501.100) and a Metrohm Double Junction reference electrode. The flow of the 3.8M potassium chloride "inner filling solution" out of the reference electrode into the test solution was measured as 1 ml in 15 hours (about 0.07 ml per hour).

The two test solutions consisted of 150 ml each of 0.05 and 1.0 moles/liter sodium chloride. The potentials so measured were 219 millivolts ("mv") and 295 mv respectively.

Sodium montmorillonite clay (4.5 g) was then added to the sodium chloride solutions to give a suspension of 30 grams/liter clay. This is nominally the amount of clay used in a drilling mud. The electrical potentials measured in the suspensions were 217 and 295 mv respectively.

Concentration is related directly to millivolts via the classical Nernst equation (the potential in mv is proportional to the logarithm of the concentration). The results indicate that the concentration of sodium ion (0.055 and 0.95 moles/liter) in each suspension is near enough identical to that in the original "pure" sodium chloride, to within 7% (this is the deviation represented by the 2 mv difference in the measurements).

Comparison A

The procedure of Example 1 was repeated, save that a conventional non-flowing reference electrode (an Orion Model 94178) was used instead of the Metrohm Double Junction flowing one. The results were very different, erroneously indicating (respectively) apparent sodium ion concentrations of 0.07 and 1.8 moles/liter.

Comparison B

A procedure similar to that of Example 1 was carried out, but again with a non-flowing reference electrode. The electrical connection between the reference electrode and the test solution was accomplished via a liquid-liquid contact at the base of the reference electrode. The particular sensor used was again an Orion Model 94178.

The calibration potential measured in 0.02 molar sodium chloride solution was 117.8 mv; the potential measured after adding 20 grams/liter montmorillonite clay was 129.2 mv. The 11.4 mv difference represents an error of 55%.

EXAMPLE 2

The experiment of Example 1 was repeated but with the Radiometer K201 reference electrode instead of the Metrohm Double Junction one. The flow rate of the internal filling solution out of this electrode was measured to be 1 ml each 10 minutes (about 6 ml per hour). Here a potential of 199.1 mv against the same sodium ion selective electrode was measured in a 0.1M sodium chloride solution.

Montmorillonite clay was added to make a suspension of 20 grams/liter solids. The electrical potential then measured between the same electrodes was 200.3 mv.

Thus, within 1 mv (4%) the concentration of sodium in the suspension was measured to be the same as in the original salt solution.

EXAMPLE 3

The experiment of Example 1 was again repeated, but with 0.1M calcium chloride in water and with a calcium ion selective electrode (Metrohm No. 6.0504.100).

The measured potential in the "pure" calcium chloride solution was 52.3 mv; in the 20 grams/liter montmorillonite suspension it was 51.2 mv.

Again, the ion selective electrode, in combination with a flowing junction reference electrode, gave a correct measurement of the amount of calcium ion in solution.

EXAMPLE 4

The Example 1 procedure was again repeated, but with a real (used) drilling mud known to contain 0.032 moles/liter sodium ion (the rest of the mud was a mixture similar to that seawater-dispersed mud described in the Table hereinbefore). The results indicated that there was 0.036 moles/liter sodium, which agrees well with the known amount.

We claim:

1. A method for the determination of a chosen ionic component of a drilling mud, in which, using an electrode selective for the chosen ion together with a reference electrode of the type having a liquid junction formed by a liquid electrolyte connectable via an aperture within the reference electrode containment vessel, there is determined the potential difference generated across the two electrodes by the ion in the mud, and thus the concentration of that ion in the mud, and in which, during the determination, the electrolyte constituting the reference electrode's liquid junction is caused to flow through the electrode containment vessel's aperture and out of the vessel into the mud.

2. The method recited in claim 1 wherein said chosen ionic component is selected from the group consisting of potassium, sodium, calcium, and magnesium cations, and chloride, sulphate, and bromide anions, and combinations thereof.

3. The method recited in claim 1 wherein said mud comprises a suspension of a bentonite clay in water.

4. The method recited in claim 1 wherein said mud contains cuttings, and further comprising the step of separating said cuttings from said mud, and wherein said electrode pair is placed in said mud after said mud has emerged from a borehole.

5. The method recited in claim 1 wherein the bridging liquid electrolyte within said reference electrode vessel flows through said vessel's aperture at a rate of at least 0.07 ml/hour.

6. The method recited in claim 1 wherein once said potential difference across said two electrodes has been measured, said ion's concentration is determined from a previously prepared calibration curve comprised of potential difference plotted against concentration.

7. The method recited in claim 1 wherein the determined ion values are thereafter employed as a basis for a calculation of the ionic components that were in the original mud at the conditions extent when the determination was effected.

* * * * *